(12) United States Patent
Spreitzer et al.

(10) Patent No.: US 6,653,438 B1
(45) Date of Patent: Nov. 25, 2003

(54) CONJUGATED POLYMERS CONTAINING SPECIAL FLUORENE STRUCTURAL ELEMENTS WITH IMPROVED PROPERTIES

(75) Inventors: Hubert Spreitzer, Viernheim (DE); Heinrich Becker Zum, Glashütten (DE); Willi Kreuder, Mainz (DE)

(73) Assignee: Covion Organic Semiconductors GmbH (DE)

( * ) Notice: Subject to any disclaimer, the term of this patent is extended or adjusted under 35 U.S.C. 154(b) by 0 days.

(21) Appl. No.: 09/806,707

(22) PCT Filed: Sep. 1, 1999

(86) PCT No.: PCT/EP99/06420

§ 371 (c)(1),
(2), (4) Date: Apr. 26, 2001

(87) PCT Pub. No.: WO00/22026

PCT Pub. Date: Apr. 20, 2000

(30) Foreign Application Priority Data

Oct. 10, 1998 (DE) .......................... 198 46 766

(51) Int. Cl.[7] ............................. C08G 79/08

(52) U.S. Cl. .................. 528/394; 528/8; 528/397; 528/488; 252/301.16; 252/301.35

(58) Field of Search ................ 528/394, 8, 397, 528/488; 252/301.16, 301.35

(56) References Cited

U.S. PATENT DOCUMENTS 5,777,070 A    7/1998  Inbasekaran et al. ....... 528/394

FOREIGN PATENT DOCUMENTS

| GB | 2313127 | 11/1997 |
|----|---------|---------|
| WO | 9705184 | 2/1997 |
| WO | 9733323 | 9/1997 |
| WO | 9954943 | 10/1999 |

*Primary Examiner*—Duc Truong
(74) *Attorney, Agent, or Firm*—Connolly Bove Lodge & Hutz LLP

(57) ABSTRACT

The invention relates to novel polymers containing fluorene structural elements, monomer parent compounds upon which said polymers are based, and the use of said inventive polymers as organic semiconductors and/or as electroluminescent material, in addition to electroluminescent devices containing said polymers.

10 Claims, No Drawings

CONJUGATED POLYMERS CONTAINING SPECIAL FLUORENE STRUCTURAL ELEMENTS WITH IMPROVED PROPERTIES

There is considerable industrial demand for large-area solid-state light sources for a number of applications, predominantly in the area of display elements, display-screen technology and illumination technology. The requirements made of these light sources cannot at present be completely satisfied by any of the existing technologies.

As an alternative to conventional display and illumination elements, such as incandescent lamps, gas-discharge lamps and non-self-illuminating liquid-crystal display elements, electroluminescent (EL) materials and devices, such as light-emitting diodes (LEDs), have already been in use for some time.

Besides inorganic electroluminescent materials and devices, low-molecular-weight, organic electroluminescent materials and devices have also been known for about 30 years (see, for example, U.S. Pat. No. 3,172,862). Until recently, however, such devices were greatly limited in their practical applicability.

WO 90/13148 and EP-A-0 443 861 describe electroluminescent devices which contain a film of a conjugated polymer as light-emitting layer (semiconductor layer). Such devices offer numerous advantages, such as the possibility of manufacturing large-area, flexible displays simply and inexpensively. In contrast to liquid-crystal displays, electroluminescent displays are self-illuminating and therefore do not require an additional illumination source at the back.

A typical device in accordance with WO 90/13148 consists of a light-emitting layer in the form of a thin, dense polymer film (semiconductor layer) containing at least one conjugated polymer. A first contact layer is in contact with a first surface, and a second contact layer is in contact with a further surface of the semiconductor layer. The polymer film of the semiconductor layer has a sufficiently low concentration of extrinsic charge carriers so that, on application of an electric field between the two contact layers, charge carriers are introduced into the semiconductor layer, the first contact layer becoming positive compared with the other layer, and the semiconductor layer emits radiation. The polymers used in such devices are conjugated. The term "conjugated polymer" is taken to mean a polymer which has a delocalized electron system along the main chain. The delocalized electron system gives the polymer semiconductor properties and enables it to transport positive and/or negative charge carriers with high mobility.

For use in EL elements as described in WO 90/13148, very many different polymers have already been proposed. Derivatives of poly(p-phenylenevinylene) (PPV) appear particularly suitable. Such polymers are described, for example, in WO 98/27136. These polymers are particularly suitable for electroluminescence in the green to red spectral region. In the blue to blue-green spectral region, the polymers proposed hitherto are principally those based on poly-p-phenylene (PPP) or polyfluorene (PF). Corresponding polymers are described, for example, in EP-A-0 707 020, WO 97/05184 and WO 97/33323. These polymers already exhibit good EL properties, although development is still not complete by far. Thus, polymers in the blue to blue-green spectral region frequently also exhibit the phenomenon of morphological instability. For example, many polyfluorenes exhibit liquid-crystalline or related behavior, which can result, in thin films, in domain formation, which is in turn unsuitable for the production of a homogeneously luminous area. These polymers also tend to form aggregates, which shifts the electroluminescence into the long-wave region in an undesired manner, and adversely affects the life of the EL elements.

The object of the present invention was therefore to provide polymers which are suitable for emission in the blue and blue-green spectral region and at the same time have improved morphological behavior.

Surprisingly, it is now been found that selection of specific substitution patterns in otherwise typical polymers principally built up from 2,7-fluorenyl units significantly improves the morphological properties without losing the very good applicational properties (emission color, quantum yield of the emission, suitability for EL applications).

The polymers according to the invention contain fluorene units whose substitution pattern makes them suitable for suppressing aggregation in the film. This is achieved in particular by the 9,9-position being substituted by two different types of aromatic radical. This result is surprising, principally in view of indications in the scientific literature (G. Klärner et al., Adv. Mater. 1998, 10, 993), according to which incorporation of diphenylfluorene units in the main chain does not give such effects. However, this also means precisely that it has proven particularly favorable to introduce two different aromatic substituents in this position.

The invention relates to conjugated polymers which contain structural units of the formula (I)

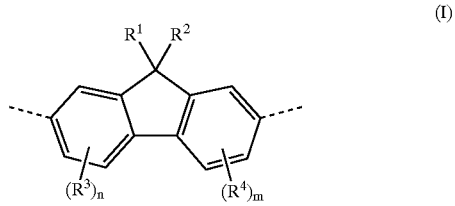

(I)

in which $R^1$ and $R^2$ are two different substituents from the group consisting of $C_2$–$C_{40}$-heteroaryl and $C_5$–$C_{40}$-aryl, where the abovementioned aryl and/or heteroaryl radicals can be substituted by one or more substituents $R^3$; for the purposes of this invention, the aryl and/or heteroaryl radicals must be of different types even if they differ through the nature or position of substituents, $R^3$ and $R^4$ are identical or different and are $C_1$–$C_{22}$-alkyl, $C_2$–$C_{20}$-heteroaryl, $C_5$–$C_{20}$-aryl, F, Cl, CN, $SO_3R^5$ or $NR^5R^6$, where the alkyl radicals can be branched or unbranched or alternatively can be cycloalkyl radicals, and individual, non-adjacent $CH_2$ groups of the alkyl radical can be replaced by O, S, C=O, COO, N—$R^5$ or simple aryl radicals, where the abovementioned aryl radicals can be substituted by one or more non-aromatic substituents $R^3$, $R^5$ and $R^6$ are identical or different and are H, $C_1$–$C_{22}$-alkyl, $C_2$–$C_{20}$-heteroaryl or $C_5$–$C_{20}$-aryl, where the alkyl radicals can be branched or unbranched or alternatively can be cycloalkyl radicals, and individual, non-adjacent $CH_2$ groups of the alkyl radical can be replaced by O, S, C=O, COO, N—$R^5$ or simple aryl radicals, where the abovementioned aryl radicals can be substituted by one or more non-aromatic substituents $R^3$, and m and n are each an integer 0, 1, 2 or 3, preferably 0 or 1.

$R^1$ and $R^2$ are preferably two different substituents from the group consisting of $C_5$–$C_{40}$-aryl and $C_2$–$C_{40}$-heteroaryl, where the above-mentioned aryl and heteroaryl radicals can be substituted by one or more substituents $R^3$.

The polymer according to invention contains at least 10 mol %, preferably from 10 mol % to 100 mol %, of structural units of the formula (I) incorporated randomly, alternately, periodically or in blocks.

The polymers according to the invention are preferably copolymers consisting of one or more structural units of the formula (I). In a further embodiment of the present invention, the polymer according to the invention may also contain different structural units of the formula (I) and further structural units which are not per se according to the invention. Examples of such further monomers are 1,4-phenylenes, 4,4'-biphenyls and further 2,7-fluorenes, which, if desired, can also carry substituents, preferably branched or unbranched $C_1$–$C_{22}$-alkyl or -alkoxy groups.

The polymers according to the invention generally have from 10 to 10000, preferably from 10 to 5000, particularly preferably from 50 to 5000, very particularly preferably from 50 to 1000, recurring units.

Particular preference is given to polymers in which m and n are zero.

The polymers according to invention can be built up by a wide variety of reactions. However, preference is given to uniform C—C coupling reactions, for example the Suzuki condensation and the Stille condensation. In this context, the term "uniform C—C coupling reaction" is taken to mean that the linking to the polymer is determined by the position of the reactive groups in the corresponding monomers. This is given particularly well by the abovementioned reactions, which are very highly suitable owing to the clean course. Also suitable is nickel-catalyzed coupling of halogenated aromatic compounds (Yamamoto coupling). Less suitable, by contrast, are oxidative processes (for example oxidative coupling using Fe(III) salts) since these result in undefined links.

The above comments also result in the preferred choice of monomers: these represent corresponding bishalogen, bispseudohalogen (i.e. in the sense of this invention e.g. bistriflate, bisnonaflate or bistosylate), bisboronic acid, bisstannate, monohalomonoboronic acid and monohalomonostannate derivatives of the compounds of the formula (I) and formula (II).

The synthesis of the polymers according to the invention is shown in illustrative terms by Scheme 1 below:

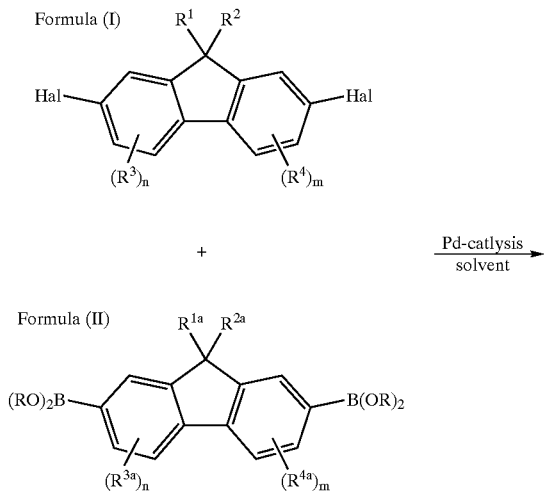

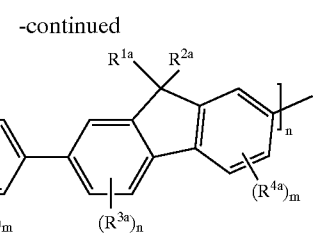

The radical R in the above scheme is hydrogen or any desired organic radical, preferably a radical having 1 to 40 carbon atoms. Examples thereof are corresponding alkyl radicals, for example methyl or butyl. Furthermore, R can be an aromatic radical having 5 to 30 carbon atoms, which can, if desired, be substituted. The radical $R^{1a}$ corresponds in its definition to the radical $R^1$; the radical $R^{2a}$ corresponds in its definition to the radical $R^2$; the radical $R^{3a}$ corresponds in its definition to the radical $R^3$; the radical $R^{4a}$ corresponds in its definition to the radical $R^4$.

Scheme 1 shows polymerization by Suzuki coupling. It is expressly pointed out that this is merely one possible embodiment. Other combinations of boronic acids and halogens/pseudohalogens are of course also feasible. The Stille polymerization can also be carried out analogously using corresponding tin compounds.

The Suzuki polymerization should be carried out as follows:

The monomers on which the structural unit of the formula (I) is based (and, if desired, further additional monomers containing corresponding active leaving groups) are reacted in an inert solvent at a temperature in the range from 0° C. to 200° C. in the presence of a palladium catalyst. It must be ensured here that the totality of all monomers used has a highly balanced ratio of boronic acid functions to halogen or pseudohalogen functions. In addition, it may prove advantageous to remove any excess reactive groups at the end of the reaction by end-capping with monofunctional reagents.

In order to carry out the above reaction with boronic acids (esters), the aromatic boron compounds, the aromatic halogen compounds, a base and catalytic amounts of the palladium catalyst are introduced into water or into one or more inert organic solvents or preferably into a mixture of water and one or more inert organic solvents, and stirred at a temperature of from 0 to 200° C., preferably from 30 to 170° C., particularly preferably from 50 to 150° C., especially preferably from 60° C. to 120° C., for a period of from 1 hour to 200 hours, preferably from 5 hours to 150 hours, particularly preferably from 24 hours to 120 hours. It may also prove advantageous here to meter in one type of monomer (for example a bisboronic acid derivative) continuously or batchwise slowly over an extended period in order thus to regulate the molecular weight. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide, dimethylacetamide and N-methylpyrrolidone, nitriles, for example acetonitrile, propionitrile and butyronitrile, and mixtures thereof.

Preferred organic solvents are ethers, such as dimethoxyethane, diethylene glycol dimethyl ether, tetrahydrofuran, dioxane, diisopropyl ether and t-butyl methyl ether, hydrocarbons, such as hexane, heptane, cyclohexane, toluene and xylene, alcohols, such as methanol, ethanol, 1-propanol, 2-propanol, 1-butanol, 2-butanol, tert-butanol and ethylene glycol, ketones, such as ethyl methyl ketone and isobutyl methyl ketone, amides, such as dimethylformamide, dimethylacetamide and N-methylpyrrolidone, and mixtures thereof.

Particularly preferred solvents are ethers, for example dimethoxyethane and tetrahydrofuran, hydrocarbons, for example cyclohexane, toluene and xylene, alcohols, for example ethanol, 1-propanol, 2-propanol, 1-butanol and tert-butanol, and mixtures thereof.

In a particularly preferred variant, water and one or more solvents are employed in the process described. Examples are mixtures of water and toluene, water, toluene and tetrahydrofuran, and water, toluene and ethanol.

Bases which are preferably used in the process described are alkali metal and alkaline earth metal hydroxides, alkali metal and alkaline earth metal carbonates, alkali metal hydrogencarbonates, alkali metal and alkaline earth metal acetates, alkali metal and alkaline earth metal alkoxides and primary, secondary and tertiary amines.

Particular preference is given to alkali metal and alkaline earth metal hydroxides, alkali metal and alkaline earth metal carbonates and alkali metal hydrogencarbonates.

Special preference is given to alkali metal hydroxides, such as sodium hydroxide and potassium hydroxide, and alkali metal carbonates and alkali metal hydrogencarbonates, such as lithium carbonate, sodium carbonate and potassium carbonate.

The base is preferably employed in the process described in a proportion of from 100 to 1000 mol %, particularly preferably from 100 to 500 mol %, very very particularly preferably from 150 to 400 mol %, especially from 180 to 250 mol %, based on boron groups.

The palladium catalyst contains palladium metal or a palladium(0) or (II) compound and a complex ligand, preferably a phosphine ligand. The two components can form a compound, for example the particularly preferred Pd(PPh3)4, or be employed separately.

Examples of suitable palladium components are palladium compounds, such as palladium ketonates, palladium acetylacetonates, nitrilopalladium halides, olefinpalladium halides, palladium halides, allylpalladium halides and palladium biscarboxylates, preferably palladium ketonates, palladium acetylacetonates, bis-$\eta^2$-olefinpalladium dihalides, palladium(II) halides, $\eta^3$-allylpalladium halide dimers and palladium biscarboxylates, very particularly preferably bis(dibenzylideneacetone)palladium(0) [Pd(dba)$_2$)], Pd(dba)$_2$ CHCl$_3$, palladium bisacetylacetonate, bis(benzonitrile) palladium dichloride, PdCl$_2$, Na$_2$PdCl$_4$, dichlorobis (dimethyl sulfoxide)palladium(II), bis(acetonitrile) palladium dichloride, palladium(II) acetate, palladium(II) propionate, palladium(II) butanoate and (1c,5c-cyclooctadienyl)palladium dichloride.

The catalyst used can likewise be palladium in metallic form, referred to below simply as palladium, preferably palladium in powdered form or on a support material, for example palladium on activated carbon, palladium on aluminum oxide, palladium on barium carbonate, palladium on barium sulfate, palladium on aluminum silicates, such as montmorillonite, palladium on SiO$_2$ and palladium on calcium carbonate, in each case having a palladium content of from 0.5 to 10% by weight. Particular preference is given to palladium in colloidal or powdered form, palladium on activated carbon, palladium on barium carbonate and/or calcium carbonate and palladium on barium sulfate, in each case having a palladium content of from 0.5 to 10% by weight. Special preference is given to palladium on activated carbon having a palladium content of 5 or 10% by weight.

The palladium catalyst is employed in the process according to invention in a proportion of from 0.01 to 10 mol %, preferably from 0.05 to 5 mol %, particularly preferably from 0.1 to 3 mol %, especially preferably from 0.1 to 1.5 mol %, based on the halogen groups.

Examples of ligands which are suitable for the process are phosphines, such as trialkylphosphines, tricycloalkylphosphines and triarylphosphines, where the three substituents on the phosphorus may be identical or different and chiral or achiral and where one or more of the ligands can link the phosphorus groups of a plurality of phosphines and where part of this link can also be one or more metal atoms.

Examples of phosphines which can be used in the process described here are trimethylphosphine, tributylphosphine, tricyclohexylphosphine, triphenylphosphine, tritolylphosphine, tris-(4-dimethylaminophenyl)phosphine, bis (diphenylphosphino)methane, 1,2-bis(diphenylphosphino) ethane, 1,3-bis(diphenylphosphino)propane and 1,1'-bis (diphenylphosphino)ferrocene.

Other suitable ligands are, for example, diketones, for example acetylacetone and octafluoroacetylacetone, and tert-amines, for example trimethylamine, triethylamine, tri-n-propylamine and triisopropylamine.

Preferred ligands are phosphines and diketones, particularly preferably phosphines.

Very particularly preferred ligands are triphenylphosphine, 1,2-bis(diphenylphosphino)ethane, 1,3-bis(diphenylphosphino)propane and 1,1'-bis(diphenylphosphino) ferrocene, in particular triphenylphosphine.

Also suitable for the process are water-soluble ligands which contain, for example, sulfonic acid salt and/or sulfonic acid radicals and/or carboxylic acid salt and/or carboxylic acid radicals and/or phosphonic acid salt and/or phosphonic acid radicals and/or phosphonium groups and/or peralkylammonium groups and/or hydroxyl groups and/or polyether groups having a suitable chain length.

Preferred classes of water-soluble ligands are phosphines substituted by the above groups, such as trialkylphosphines, tricycloalkylphosphines, triarylphosphines, dialkylarylphosphines, alkyldiarylphospines and heteroarylphosphines, such as tripyridylphosphine and trifurylphosphine, where the three substituents on the phosphorus may be identical or different and chiral or achiral and where one or more of the ligands can link the phosphorus groups of a plurality of phosphines and where part of this link can also be one or more metal atoms, phosphites, phosphinates and phosphonates, phosphols, dibenzophosphols, and cyclic and oligo- and polycyclic compounds containing phosphorus atoms.

The ligand is employed in the process in a proportion of from 0.1 to 20 mol %, preferably from 0.2 to 15 mol %, particularly preferably from 0.5 to 10 mol %, especially preferably from 1 to 6 mol %, based on the aromatic halogen groups. It is also possible, if desired, to employ mixtures of two or more different ligands.

Advantageous embodiments of the Suzuki variant of the process are described for low-molecular-weight couplings in, for example, WO 94/10105, EP-A-679 619, WO-A-694 530 and PCT/EP 96/03154, which are expressly incorporated herein by way of reference.

The Stille polymerization should be carried out as follows:

The monomers on which the structural units of the formulae (I) and (II) are based (and, if necessary, further monomers containing corresponding active leaving groups) are reacted in an inert solvent at a temperature in range from 0° C. to 200° C. in the presence of a palladium-containing catalyst. It must be ensured here that the totality of all monomers used has a highly balanced ratio of organotin functions to halogen or pseudohalogen functions. In addition, it may prove advantageous to remove any excess reactive groups at the end of the reaction by end-capping with monofunctional reagents.

A review of this reaction is given, for example, in J. K. Stille, Angew. Chemie Int. Ed. Engl. 1986, 25, 508.

In order to carry out the process, aromatic tin compounds and aromatic halogen compounds are preferably introduced into one or more inert organic solvents and stirred at a temperature of from 0 to 200° C., preferably from 30 to 170° C., particularly preferably from 50 to 150° C., especially preferably from 60° C. to 120° C., for a period of from 1 hour to 200 hours, preferably from 5 hours to 150 hours, particularly preferably from 24 hours to 120 hours. It may also prove advantageous here to meter in one type of monomer (for example a bisstannyl derivative) continuously or batchwise slowly over an extended period in order thus to regulate the molecular weight. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

Preferred organic solvents are ethers, such as dimethoxyethane, diethylene glycol dimethyl ether, tetrahydrofuran, dioxane and diisopropyl ether, hydrocarbons, such as hexane, heptane, cyclohexane, benzene, toluene and xylene, alcohols, such as methanol, ethanol, 1-propanol, 2-propanol, 1-butanol, 2-butanol, tert-butanol and ethylene glycol, ketones, such as ethyl methyl ketone, and amides, such as DMF.

Particularly preferred solvents are amides, very particularly preferably DMF.

The palladium and phosphine components should be selected analogously to the description for the Suzuki variant.

The present invention furthermore relates to the monomeric precursors on which the polymers according to the invention are based. These are given by the formula (A)

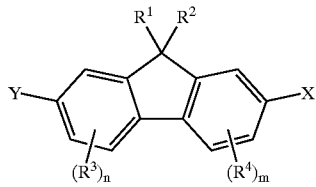

in which

R$^1$ and R$^2$ are two different substituents from the group consisting of C$_2$–C$_{40}$-heteroaryl and C$_5$–C$_{40}$-aryl, where the abovementioned aryl and heteroaryl radicals can be substituted by one or more substituents R$^3$; for the purposes of this invention, the aryl and heteroaryl radicals must be of different types even if they differ through the nature or position of substituents, R$^3$ and R$^4$ are identical or different and are C$_1$–C$_{22}$-alkyl, C$_2$–C$_{20}$-heteroaryl, C$_5$–C$_{20}$-aryl, F, Cl, CN, SO$_3$R$^5$ or NR$^5$R$^6$, where the alkyl radicals can be branched or unbranched or alternatively can be cycloalkyl radicals, and individual, non-adjacent CH$_2$ groups of the alkyl radical can be replaced by O, S, C=O, COO, N—R$^5$ or simple aryl radicals, where the abovementioned aryl radicals can be substituted by one or more non-aromatic substituents R$^3$, R$^5$ and R$^6$ are identical or different and are H, C$_1$–C$_{22}$-alkyl, C$_2$–C$_{20}$-heteroaryl or C$_5$–C$_{20}$-aryl, where the alkyl radicals can be branched or unbranched or alternatively can be cycloalkyl radicals, and individual, non-adjacent CH$_2$ groups of the alkyl radical can be replaced by O, S, C=O, COO, N—R$^5$ or simple aryl radicals, where the abovementioned aryl radicals can be substituted by one or more non-aromatic substituents R$^3$, m and n are each an integer 0, 1, 2 or 3, preferably 0 or 1, X and Y are identical or different and are halogen, preferably Cl, Br or I, B(OR$^7$)$_2$ or SnR$^7$R$^8$R$^9$, and R$^7$, R$^8$ and R$^9$ are identical or different and are H or C$_1$–C$_6$-alkyl, where two radicals can also form a common ring and these radicals can also be branched or unbranched.

Examples of monomers are shown in Scheme 2 below:

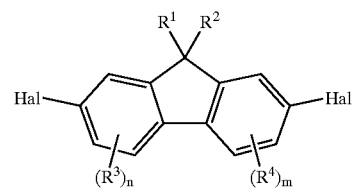

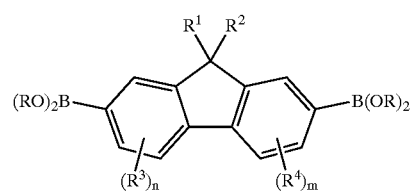

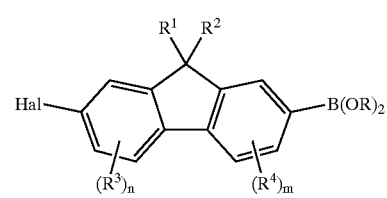

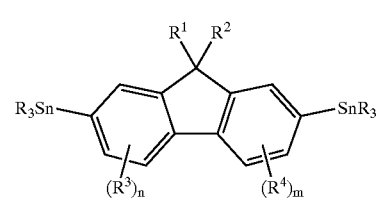

The suitable 9-Aryl$^1$-9-Aryl$^2$-fluorene monomers can be synthesized, for example, as described in Scheme 3 below:

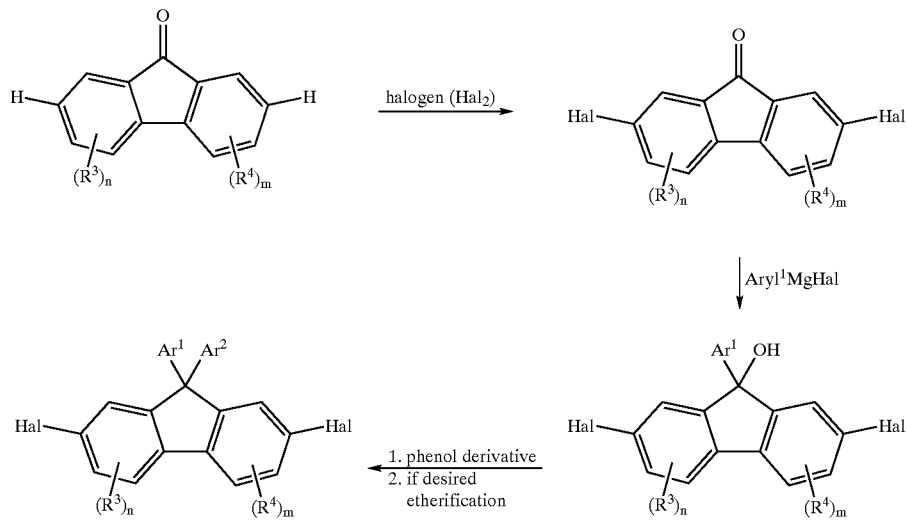

In the above formulae, $Ar^1$ is a radical $R^1$ and $Ar^2$ is a radical $R^2$.

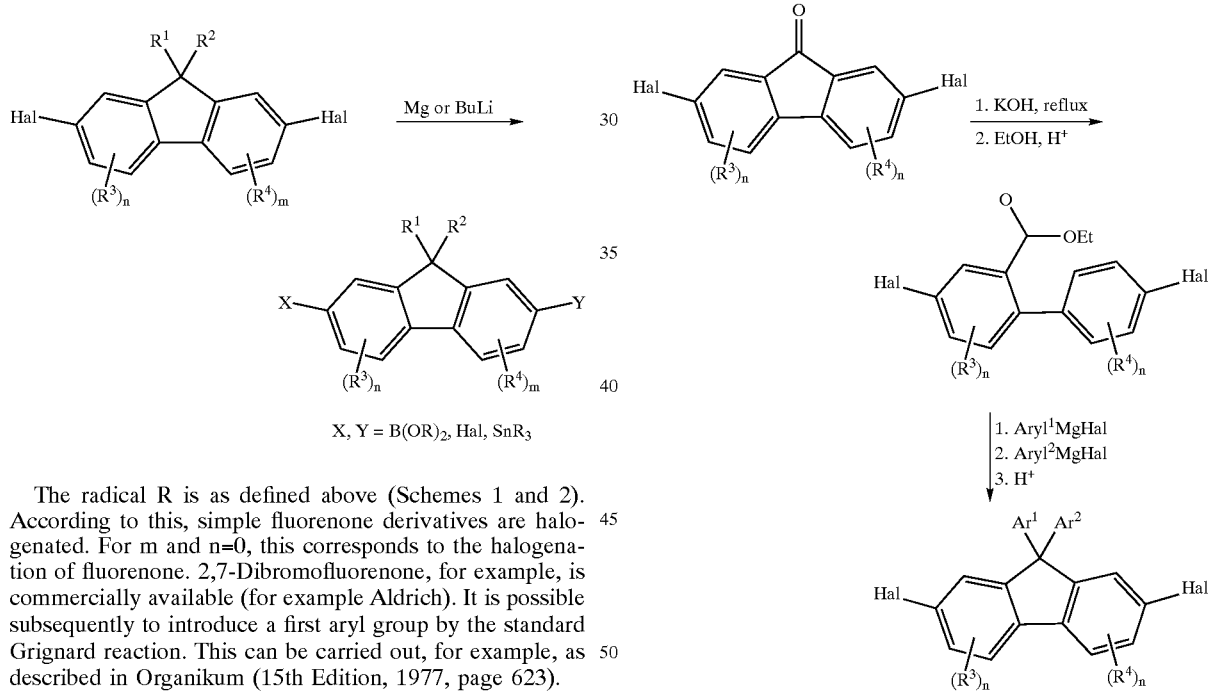

X, Y = B(OR)$_2$, Hal, SnR$_3$

The radical R is as defined above (Schemes 1 and 2). According to this, simple fluorenone derivatives are halogenated. For m and n=0, this corresponds to the halogenation of fluorenone. 2,7-Dibromofluorenone, for example, is commercially available (for example Aldrich). It is possible subsequently to introduce a first aryl group by the standard Grignard reaction. This can be carried out, for example, as described in Organikum (15th Edition, 1977, page 623).

A phenol derivative can subsequently be added on with acid catalysis. This can be carried out analogously to the descriptions in WO 92/07812. The resultant compound can be etherified. This can be carried out, for example, by the Williamson method (cf. Organikum, 15th Edition, 1977, page 253).

The resultant compounds (bishalofluorene derivatives) can be used as monomers as they are. Further reaction (metallation with subsequent reaction either with borates or trialkyltin halide) enables further monomers to be obtained: fluorenebisboronic acid derivatives, fluorene bisstannates or, with corresponding stoichiometry, also monohalofluorenemonoboronic acid derivatives or monohalofluorene monostannates. This last-mentioned reaction can be carried out by standard methods, as described, for example, in WO 98/27136.

Another method is shown in the following scheme:

The radicals here are defined as $Aryl^1 = Ar^1 = R^1$ and $Aryl^2 = Ar^2 = R^2$.

Starting from bishalogenated fluorenone derivatives (see above), firstly 4,4'-dihalobiphenyl-2-carboxylate derivatives can be obtained as intermediate by basic ring-opening with subsequent esterification. These compounds can then be converted into the desired fluorene monomers by reaction with two different aryl-Grignard reagents, where interim hydrolysis in order to isolate the corresponding ketone as intermediate has proven helpful, followed by acidic cyclization.

As already mentioned above, a further reaction is also possible here to give the corresponding fluorenebisboronic acid derivatives, fluorene bisstannates or monohalofluorenemonoboronic acid derivatives or monohalofluorene monostannates.

This has shown that monomers which are preferably converted into polymers according to invention by the polymerization methods described above are readily accessible.

The polymers obtained in this way are very particularly preferably suitable as organic semiconductors and in particular as electroluminescent materials.

For the purposes of the present invention, the term "electroluminescent materials" is taken to mean materials which can be used as the active layer in an electroluminescent device. "Active layer" means that the layer is capable of emitting light on application of an electric field (light-emitting layer) and/or that it improves the injection and/or transport of positive and/or negative charges (charge injection or charge transport layer).

The invention therefore also relates to the use of a polymer according to the invention as electroluminescent material and as organic semiconductor.

In order to be used as electroluminescent materials, the polymers according to invention are generally applied to a substrate in the form of a film by known methods which are customary to the person skilled in the art, such as dipping or spin coating.

The invention thus likewise relates to an electroluminescent device having one or more active layers, where at least one of these active layers comprises one or more polymers according to the invention. The active layer can be, for example, a light-emitting layer and/or transport layer and/or a charge injection layer.

The general construction of such electroluminescent devices is described, for example, in U.S. Pat. No. 4,539,507 and U.S. Pat. No. 5,151,629. Electroluminescent devices containing polymers are described, for example, in WO 90/13148 and EP-A-0 443 861.

They usually contain an electroluminescent layer between a cathode and an anode, at least one of the electrodes being transparent. In addition, one or more electron injection and/or electron transport layers can be installed between the electroluminescent layer and the cathode and/or one or more hole injection and/or hole transport layers can be installed between the electroluminescent layer and the anode. The cathode can preferably be a metal or metallic alloy, for example Ca, Sr, Ba, Mg, Al, In or Mg/Ag. The anode can be a metal, for example Au, or another substance which conducts in a metallic manner, such as an oxide, for example ITO (indium oxide/tin oxide), on a transparent substrate, for example of glass or transparent polymer.

In operation, the cathode is set to a negative potential compared with the anode. Electrons are injected by the cathode into the electron injection layer/electron transport layer or directly into the light-emitting layer. At the same time, holes are injected by the anode into the hole injection layer/hole transport layer or directly into the light-emitting layer.

The injected charge carriers move toward one another through the active layers under the influence of the applied voltage. This results in electron/hole pairs at the interface between the charge transport layer and the light-emitting layer or within the light-emitting layer; these pairs recombine with emission of light. The color of the emitted light can be varied through the materials used as light-emitting layer.

Electroluminescent devices are used, for example, as self-illuminating display elements, such as control lamps, alphanumeric displays, monochromic or multichromic matrix displays, signs, electro-optical storage media and in opto-electronic couplers.

Various documents are cited in the present application, in order, for example, to illustrate the technical background to the invention. All these documents are expressly incorporated herein by way of reference.

The invention is described in greater detail by the examples, without this being intended to represent a limitation.

A) Synthesis of the Monomers

1. Preparation of the monomers according to the invention:

EXAMPLE M1

Preparation of 2,7-Dibromo-9-(2,5-dimethylphenyl)-9-[4-(3,7-dimethyloctyloxy)phenyl]fluorene i) 2,7-Dibromo-9-(2,5-dimethylphenyl)fluoren-9-ol:

The Grignard reagent made from 102 g of bromo-p-xylene, prepared in the customary manner in THF, was added dropwise to a suspension of 2,7-dibromofluorenone (169 g) in 500 ml of THF at 5–15° C. The batch was subsequently refluxed for two hours. For hydrolysis, about 1200 ml of ice-water and 30 ml of concentrated sulfuric acid were added. The phases were separated, the aqueous phase was back-shaken a number of times with ethyl acetate, and the combined organic phases were back-shaken again with water. After drying over $Na_2SO_4$, the solvent was removed, and the resultant crude product was recrystallized from ethanol.

Yield: 163 g (73%). $^1$H-NMR ($d_6$-DMSO): [ppm] δ=8.05 (s (br), 1H, OH), 7.85 (d, 2H, H-4, J=8 Hz), 7.60 (dd, 2H, H-3, $J_1$=1 Hz, $J_2$=8 Hz), 7.15 (d, 2H, H-1, J=2 Hz), 7.02 (dd (br), 1H, H-4', $J_1$=2 Hz, $J_2$=8 Hz), 6.85 (d, 1H, H-3', J=7.5 Hz), 6.48 (s (br), 1H, H-6'), 2.38 (s, 3H, Me), 1.2 (s (br), 3H, Me).

ii) 2,7-Dibromo-9-(2,5-dimethylphenyl)-9-(4-hydroxyphenyl)fluorene 9.5 g of phenol were mixed with 22.2 g of 2,7-dibromo-9-(2,5-dimethylphenyl)fluoren-9-ol, 25 ml of toluene and 0.1 ml of mercapto-propionic acid. 5 ml of concentrated sulfuric acid were subsequently added dropwise. The batch was then stirred at 60° C. for about 2 hours, and finally 100 ml of MeOH and 100 ml of water were added. The solid was filtered off with suction and further purified by stirring with ethanol.

Yield: 16 g (61%). $^1$H-NMR ($d_6$-DMSO): [ppm] δ=9.4 (s (br), 1H, OH), 7.92 (d, 2H, H-4, J=8 Hz), 7.60 (dd, 2H, H-3, $J_1$=1 Hz, $J_2$=8 Hz), 7.45 (d, 2H, H-1, J=2 Hz), 6.98 (m, 4H, H-2", H-3', H-4'), 6.87 (s (br), 1H, H-6'), 6.67 (part of an M'BB', 2H, H-3"), 2.17 (s, 3H, Me), 1.38 (s(br), 3H, Me).

iii) 2,7-Dibromo-9-(2,5-dimethylphenyl)-9-[4-(3,7-dimethyloctyloxy)phenyl]-fluorene 52 g of 2,7-dibromo-9-(2,5-dimethylphenyl)-9-(4-hydroxyphenyl)fluorene were refluxed with 18 g of 3,7-dimethyloctyl chloride, 80 ml of ethanol, 7 g of KOH and 1 g of NaI for 5 days. According to TLC, the reaction was complete after this time. The solvent was stripped off, ethyl acetate was added, and the precipitate was filtered off with suction and rinsed a number of times with ethyl acetate. The organic phase was dried, and the solvent was stripped off.

The product was purified by bidistillation in a short-path evaporator ($10^{-3}$ mbar; 1st distillation for drying: 80° C.; 2nd distillation: 250° C.).

Yield: 48 g (73%). $^1$H-NMR (CDCl$_3$): [ppm] δ=7.83 (d, 2H, H-4, J=8 Hz), 7.55 (dd, 2H, H-3, $J_1$=1 Hz, $J_2$=8 Hz), 7.38 (d, 2H, H-1, J=2 Hz), 7.02 (m, 4H, H-2", H-3', H-4'), 6.92 (s (br), 1H, H-6'), 6.77 (part of an M'BB', 2H, H-3"), 3.90 (m, 2H; $OCH_2$), 2.17 (s, 3H, Me), 1.80 (m, 1H), 1.65 (m, 3H), 1.38 (s (br), 3H, Me), 1.30 (m, 3H); 1.16 (m, 3H), 0.93 (d, 3H, $CH_3$, J=6.6 Hz), 0.86 (d, 6H; 2×$CH_3$, J=6.7 Hz).

EXAMPLE M2

Preparation of Bisethylene Glycol 9-(4-(3,7-Dimethyloctyloxy)phenyl)-9-(2,5-dimethylphenyl)fluorene-2,7-bisboronate Under a nitrogen atmosphere, (86.0 g, 130 mmol) of 2,7-dibromo-9-(4-(3,7-dimethyloctyloxy)phenyl)-9-(2,5-dimethylphenyl)fluorene were dissolved in 300 ml of distilled THF, and the solution was added dropwise to 7.29 g (300 mmol) of magnesium with gentle warming. The mixture was subsequently refluxed for 3 hours. The mixture was then diluted with 100 ml of distilled THF and cooled to room temperature. 34.3 g (330 mmol) of trimethyl borate were dissolved in 500 ml of distilled THF in a 2 l flask and cooled to −78° C. The Grignard solution was slowly added dropwise at this temperature at such a rate that the temperature did not exceed −70° C. (2 hours). The mixture was slowly warmed to room temperature overnight with stirring.

500 ml of ice-water and 32.5 ml of concentrated sulfuric acid were added to the jelly-like material (greenish), the mixture was stirred for 60 minutes, and the organic phase was separated off. The water phase was extracted once with 100 ml of ethyl acetate. The organic phases were combined and washed with saturated NaCl, dried over MgSO$_4$ and evaporated in a rotary evaporator, giving 88.1 g of crude product. This was suspended twice in 400 ml of n-hexane, stirred at RT for 60 minutes, filtered off with suction and dried at RT in a vacuum drying cabinet (yield 67.5 g). The boronic acid was dissolved in 450 ml of dichloromethane, and 13 g of ethylene glycol and 0.8 ml of sulfuric acid were added. The mixture was refluxed for 5 hours on a water separator, cooled, washed with 100 ml of water (these phases were extracted with 150 ml of dichloromethane) and dried using MgSO$_4$. The product was evaporated in a rotary evaporator, and the residue was recrystallized twice from a mixture of 600 ml of n-hexane and 70 ml of ethyl acetate, giving 24.5 g (32%) of bisethylene glycol 9-(4-(3,7-dimethyloctyloxy)phenyl)-9-(2,5-dimethylphenyl)fluorene-2,7-bisboronate as colorless crystals with a purity (NMR) of greater than 99%.

$^1$H-NMR (CDCl$_3$): [ppm] δ=7.95–7.75 (m, 6H, fluorene); 7.17 (d, 2H, J=8 Hz, H-2'); 6.95 (br. s, 1H, H-2"); 6.90 (d, 1H, J=8 Hz, H-4"); 6.84 (d, 1H, J=8 Hz, H-5"); 4.34, (s, 8H, boronate); 3.95–3.85 (m, 2H, OCH$_2$); 2.20 (s, 3H, CH$_3$); 1.80–1.45 (m, 4H); 1.35 (3H, CH$_3$); 1.32–1.10 (m, 6H, alkyl); 0.90 and 0.85 (2d, 9H, 3×CH$_3$).

2. Preparation of Further Comonomers:

EXAMPLE CM1

Preparation of 2,7-Dibromo-9,9-bis(2-ethylhexyl)fluorene

The preparation was carried out analogously to Example 1 of WO 97/05184. The product (84% yield) was isolated as a high-viscosity, pale yellow oil by bidistillation in a short-path evaporator [10$^{-3}$ mbar; 1st distillation (for removing excess ethylhexyl bromide and residual DMSO) 100° C.; 2nd distillation: 155° C.].

$^1$H-NMR (CDCl$_3$): [ppm] δ=7.54–7.43 (m, 6H, H-aryl); 1.93 (d with Fs., 4H, J=4.0 Hz); 1.0–0.65 (m, 22H, H-alkyl); 0.58–0.45 (m, 8H, H-alkyl).

EXAMPLE CM2

Preparation of Bisglycol 9,9-bis(2-Ethylhexyl)fluorene-2,7-bisboronate

Magnesium (6.32 g, 0.26 mol) was initially introduced in 10 ml of THF, a little iodine was added, and a few drops of 2,7-dibromo-9,9-bis(2-ethylhexyl)fluorene were added. The initiation of the reaction was evident from considerable exothermicity. The remainder of the bisbromide (a total of 68.56 g, 0.125 mol) and 300 ml of THF were subsequently added dropwise in parallel. When the addition was complete, the mixture was refluxed for about 5 hours. Small amounts of Mg turnings were still evident. In parallel, trimethyl borate (28.6 g, 0.27 mol) in THF (200 ml) was initially introduced and cooled to −70° C. At this temperature, the Grignard solution was slowly added dropwise. The mixture was subsequently slowly warmed to room temperature overnight with stirring.

The reaction solution was added to 300 ml of ice-water and 10 ml of concentrated sulfuric acid, and the organic phase was separated off. The organic phase was then washed (neutral) once with water. After drying over Na$_2$SO$_4$, the mixture was evaporated in a rotary evaporator. The crude product was stirred with hexane (500 ml). This gave the crude bisboronic acid (containing variable amounts of various anhydrides).

This was esterified directly by refluxing (12 hours) in toluene with ethylene glycol and sulfuric acid on a water separator.

Yield over the two steps: 70–85%. Purity (NMR)>98.5% $^1$H-NMR (CDCl$_3$): (NMR signals greatly broadened or doubled due to diastereomerism) δ=7.86 (m, 2H, H-1), 7.79 (m, 2H, H-3), 7.73 (d, 2H, H-4, J=8 Hz), 4.38 (s (br), 8H, O—CH$_2$), 2.02 (m, 4H, C—CH$_2$—), 0.75 (m (br), 22H, H-alkyl), 0.47 (m (br), 8H, H-alkyl).

EXAMPLE CM3

Preparation of 4,4'-Dibromotriphenylamine

The preparation was carried out analogously to K. Haga et al, Bull. Chem. Soc. Jpn., 1986, 59, 803–7: 3.10 g (10.4 mmol) of bis(4-bromophenyl)amine (J. Berthelot et al, Can. J. Chem., 1989, 67, 2061), 1.28 g of cyclohexane-1,4-dione (11.4 mmol) and 2.17g (11.4 mmol) of p-toluenesulfonic acid hydrate were heated in 50 ml of toluene on a water separator. After a reaction time of 12 hours, the solvent was removed and the product was purified by column chromatography (hexane/ethyl acetate 4:1). 3.82 g (9.46 mmol, 91%) of 4,4'-dibromotriphenylamine were obtained as a viscous oil.

$^1$H-NMR (CDCl$_3$): [ppm] δ=7.01–6.95 (m, 5H), 6.88, 6.74 (AA'BB', 4+4H).

B) Synthesis of the Polymers:

EXAMPLE P1

Copolymerization of Bisglycol 9,9-bis(2-Ethylhexyl)fluorene-2,7-bisboronate and 2,7-Dibromo-9-(2,5-dimethylphenyl)-9-(4-(3,7-dimethyloctyloxy)phenyl)fluorene by the Suzuki Reaction (Polymer P1)

13.21 g (20 mmol) of 2,7-dibromo-9-(2,5-dimethylphenyl)-9-(4-(3,7-dimethyloctyloxy)phenyl)fluorene and 11.61 g of K$_2$CO$_3$ (84 mmol) were dissolved in 25 ml of toluene and 25 ml of water and aerated with N$_2$. 7.743 g (14.6 mmol) of bisglycol 9,9-bis(2-ethylhexyl)fluorene-2,7-bisboronate and 200 mg of Pd(PPh$_3$)$_4$ (0.17 mmol) were added under a protective gas. The yellow-brownish, cloudy suspension was stirred vigorously at an internal temperature of 87° C. under an N$_2$ blanket. On each of the following three days, 1.11 g (2.1 mmol) of the diboronate were added. After 3 days, a further 25 ml of toluene were added to the very viscous mixture. After a total of 4 days, the mixture was worked up.

The reaction solution was diluted with 150 ml of toluene, and the solution was stirred for 3 hours with 200 ml of 2% aqueous NaCN. During this operation, the mixture became almost completely colorless. The batch was transferred into a separating funnel under a protective gas. The organic phase with washed with $H_2O$ and precipitated by addition to 500 ml of ethanol.

The polymer was dissolved in 635 ml of THF at 40° C. for 1 hour and precipitated using 640 ml of MeOH, washed and dried under reduced pressure (10.13 g). The product was re-precipitated again from 405 ml of THF/400 ml of methanol, filtered off with suction and dried to constant weight, giving 7.55 g (42%) of polymer P1 as a pale yellow solid.

$^1$H-NMR (CDCl$_3$): [ppm] δ=8.1–6.3 (m, 19H, H-fluorene, H-phenyl); 4.0 (m, 2H, OCH$_2$); 2.3–0.4 (m, 59H, alkyl+ alkoxy-H). GPC: THF+0.25% oxalic acid; column set SDV500, SDV 1000, SDV10000 (PPS), 35° C., UV detection 254 nm: $M_w$=156000 g/mol, $M_n$=88000 g/mol. UV-VIS (film): $\lambda_{max}$=372 nm; PL (film): $\lambda_{max}$=413 nm, 433 nm.

EXAMPLE P2

Copolymerization of Bisethylene Glycol 9-(4-(3,7-Dimethyloctyloxy)phenyl)-9-(2,5-dimethylphenyl) fluorene-2,7-bisboronate, 2,7-Dibromo-9-(2,5-dimethylphenyl)-9-(4-(3,7-dimethyloctyloxy)phenyl) fluorene and 1 mol-% of 4,4'-Dibromotriphenylamine by the Suzuki Reaction (Polymer P2)

6.4733 g (9.8 mmol) of 2,7-dibromo-9-(2,5-dimethylphenyl)-9-(4-(3,7-dimethyloctyloxy)phenyl) fluorene, 6.4246 g (10.00 mmol) of bisethylene glycol 9-(4-(3,7-dimethyloctyloxy)phenyl)-9-(2,5-dimethylphenyl)fluorene-2,7-bisboronate, 80.6 mg (0.2 mmol) of 4,4'-dibromotriphenylamine, 9.67 g (42 mmol) of K$_3$PO$_4$ hydrate, 30 ml of toluene, 15 ml of water and 0.25 ml of ethanol were degassed for 30 minutes by passing N$_2$ through the mixture. 175 mg (0.15 mmol) of Pd(PPh$_3$)$_4$ were subsequently added under a protective gas. The suspension was stirred vigorously at an internal temperature of 87° C. (gentle reflux) under an N$_2$ blanket. After 4 days, a further 0.30 g of bisethylene glycol 9-(4-(3,7-dimethyloctyloxy) phenyl)-9-(2,5-dimethylphenyl)fluorene-2,7-bisboronate were added. After the mixture had been heated for a further 6 hours, 0.3 ml of bromobenzene was added, and the mixture was refluxed for a further 3 hours.

The reaction solution was diluted with 200 ml of toluene, and the solution was stirred for 3 hours with 200 ml of 2% aqueous NaCN. During this operation, the mixture became almost completely colorless. The organic phase was washed with H$_2$O and precipitated by addition to 800 ml of ethanol.

The polymer was dissolved in 200 ml of THF at 40° C. for 1 hour and precipitated using 250 ml of MeOH, washed and dried under reduced pressure. The product was re-precipitated again from 200 ml of THF/250 ml of methanol, filtered off with suction and dried to constant weight, giving 9.3 g (18.5 mmol, 93%) of polymer P2 as a pale yellow solid.

$^1$H-NMR (CDCl$_3$): [ppm] δ=7.8 (m, 2H, fluorene); 7.55 (br. s; 4H, fluorene) 7.15 (br. s, 2H phenyl); 7.0–6.9 (m, 3H, 2,5-dimethylphenyl); 6.7 (br. s, 2H, phenyl), 3.95 (br. s, 2H, OCH$_2$), 2.1 (s, 3H, CH$_3$); 1.7 (m, 1H, alkyl); 1.6 (s, 3H, CH$_3$); 1.5–0.8 (m, 18H, alkyl). GPC: THF+0.25% oxalic acid; column set SDV500, SDV 1000, SDV10000 (PPS), 35° C., UV detection 254 nm: $M_w$=43000 g/mol, $M_n$=23000 g/mol. Electroluminescence: $\lambda_{max}$=448 nm; result at max. eff.: 0.44 cd/A at 6.7 V/46.9 mA/cm$^2$/202 cd/m$^2$. 100 cd/m$^2$ was achieved at a voltage of 6.3 V and a current density of 24.4 mA/cm$^2$.

EXAMPLE P3

Polymerization of Bisethylene Glycol 9-(4-(3,7-Dimethyloctyloxy)phenyl)-9-(2,5-dimethylphenyl) fluorene-2,7-bisboronate and 2,7-Dibromo-9-(2,5-dimethylphenyl)-9-(4-(3,7-dimethyloctyloxy)phenyl) fluorene by the Suzuki Reaction (Polymer P3)

Analogously to Example P2, 6.6054 g (10.00 mmol) of 2,7-dibromo-9-(2,5-dimethylphenyl)-9-(4-(3,7-dimethyloctyloxy)phenyl)fluorene, 6.4246 g (10.00 mmol) of bisethylene glycol 9-(4-(3,7-dimethyloctyloxy)phenyl)-9-(2,5-dimethylphenyl)fluorene-2,7-bisboronate and 9.67 g (42 mmol) of K$_3$PO$_4$ hydrate were polymerized in 30 ml of toluene, 15 ml of water and 0.25 ml of ethanol with the aid of 175 mg (0.15 mmol) of Pd(PPh$_3$)$_4$. End-capping, analogous work-up and purification gave 9.1 g (18.2 mmol, 91%) of polymer P3 as a pale yellow solid.

$^1$H-NMR (CDCl$_3$): [ppm] δ≦7.8 (m, 2H, fluorene); 7.55 (br. s; 4H, fluorene) 7.15 (br. s, 2H phenyl); 7.0–6.9 (m, 3H, 2,5-dimethylphenyl); 6.7 (br. s, 2H, phenyl), 3.95 (br. s, 2H, OCH$_2$), 2.1 (s, 3H, CH$_3$); 1.7 (m, 1H, alkyl); 1.6 (s, 3H, CH$_3$); 1.5–0.8 (m, 18H, alkyl). GPC: THF+0.25% oxalic acid; column set SDV500, SDV 1000, SDV10000 (PPS), 35° C., UV detection 254 nm: $M_w$=47000 g/mol, $M_n$=27000 g/mol. Electroluminescence: $\lambda_{max}$=447 nm; result at max. eff.: 0.18 cd/A at 7.2 V/57.3 mA/cm$^2$. 100 cd/m$^2$ was achieved at a voltage of 7.3 V and a current density of 62.1 mA/cm$^2$.

EXAMPLE P4

Polymerization of Bisethylene Glycol 9-(4-(3,7-Dimethyloctyloxy)phenyl)-9-(2,5-dimethylphenyl) fluorene-2,7-bisboronate, 2,7-Dibromo-9-(2,5-dimethylphenyl)-9-(4-(3,7-dimethyloctyloxy)phenyl) fluorene and 3% of 4,4'-Dibromotriphenylamine by the Suzuki Reaction (Polymer P4)

Analogously to Example P2, 9.328 g (14.10 mmol) of 2,7-dibromo-9-(2,5-dimethylphenyl)-9-(4-(3,7-dimethyloctyloxy)phenyl)fluorene, 7.955 g (15.00 mmol) of bisethylene glycol 9,9-bis(2-ethylhexyl)fluorene-2,7-bisboronate, 362.8 mg (0.9 mmol) of 4,4'-dibromotriphenylamine and 8.71 g (62 mmol) of K$_2$CO$_3$ were polymerized in 30 ml of toluene, 15 ml of water and 0.3 ml of ethanol with the aid of 260 mg (0.225 mmol) of Pd(PPh$_3$)$_4$. End-capping, analogous work-up and purification gave 11.1 g (24.9 mmol, 83%) of polymer P4 as a pale yellow solid.

$^1$H-NMR (CDCl$_3$): [ppm] δ=7.85 (m, 1H fluorene); 7.75–7.45 (br. m; 4H, fluorene); 7.28 (m, 1H, fluorene); 7.1 (br. s, 1H phenyl); 7.0–6.9 (m, 1.5H, 2,5-dimethylphenyl); 6.75 (br. s, 2H, phenyl), 3.95 (br. s, 1H, OCH$_2$), 2.23 (s, 2H, CH$_2$); 2.1–0.5 (m, 27.5H, alkyl). GPC: THF+0.25% oxalic acid; column set SDV500, SDV 1000, SDV10000 (PPS), 35° C., UV detection 254 nm: $M_w$=47000 g/mol, $M_n$=27000 g/mol. Electroluminescence: $\lambda_{max}$=446 nm; PL: $\lambda_{max}$=425, 452 nm; result at max. eff.: 0.36 cd/A at 7.5 V174.3 mA/cm$^2$/271 cd/m$^2$. 100 cd/m$^2$ was achieved at a voltage of 6.6 V and a current density of 30.6 mA/cm$^2$.

EXAMPLE P5

Polymerization of Bisethylene Glycol 9-(4-(3,7-Dimethyloctyloxy)phenyl)-9-(2,5-dimethylphenyl)fluorene-2,7-bisboronate, 2,7-Dibromo-9-(2,5-dimethylphenyl)-9-(4-(3,7-dimethyloctyloxy)phenyl)fluorene and 1% of 4,4'-Dibromotriphenylamine by the Suzuki Reaction (Polymer P5)

Analogously to Example P2, 12.966 g (19.6 mmol) of 2,7-dibromo-9-(2,5-dimethylphenyl)-9-(4-(3,7-dimethyloctyloxy)phenyl)fluorene, 10.607 g (20.00 mmol) of bisethylene glycol 9,9-bis(2-ethylhexyl)fluorene-2,7-bisboronate, 161 mg (0.4 mmol) of 4,4'-dibromotriphenylamine and 11.61 g (84 mmol) of $K_2CO_3$ were polymerized in 40 ml of toluene, 20 ml of water and 0.5 ml of ethanol with the aid of 350 mg (0.3 mmol) of $Pd(PPh_3)_4$. End-capping, analogous work-up and purification gave 12.2 g (27.4 mmol, 68%) of polymer P5 as a pale yellow solid.

$^1$H-NMR ($CDCl_3$): [ppm] δ=7.85 (m, 1H fluorene); 7.75–7.45 (br. m; 4H, fluorene); 7.28 (m, 1H, fluorene); 7.1 (br. s, 1H phenyl); 7.0–6.9 (m, 1.5H, 2,5-dimethylphenyl); 6.75 (br. s, 2H, phenyl), 3.95 (br. s, 1H, $OCH_2$), 2.23 (s, 2H, $CH_2$); 2.1–0.5 (m, 27.5H, alkyl). GPC: THF+0.25% oxalic acid; column set SDV500, SDV 1000, SDV10000 (PPS), 35° C., UV detection 254 nm: $M_w$=53000 g/mol, $M_n$=31000 g/mol. Electroluminescence: $\lambda_{max}$=446 nm; PL: $\lambda_{max}$=425, 452 nm; result at max. eff.: 0.14 cd/A at 5.7V/77.0 mA/cm$^2$/110 cd/m$^2$. 100 cd/m$^2$ was achieved at a voltage of 5.7 V and a current density of 83.0 mA/cm$^2$.

COMPARATIVE EXAMPLES

EXAMPLE C1

Suzuki Polymerization of 2,7-Dibromo-9,9-bis(2-ethylhexyl)fluorene and Bisglycol 9,9-bis(2-Ethylhexyl)fluorene-2,7-bisboronate (Polymer C1), Preparation of Poly-2,7-[9,9-bis(2-ethylhexyl)fluorene]

8.227 g (15.00 mmol) of 2,7-dibromo-9,9-bis(2-ethylhexyl)fluorene, 7.956 g (15.00 mmol) of diethylene glycol 9,9-bis(2-ethylhexyl)fluorene-2,7-bisboronate, 8.71 g (63 mmol) of $K_2CO_3$, 25 ml of toluene and 15 ml of water were degassed for 30 min by passing $N_2$ through the mixture. 230 mg (0.2 mmol) of $Pd(PPh_3)_4$ were subsequently added under a protective gas. The suspension was stirred vigorously at an internal temperature of 87° C. (gentle reflux) under an $N_2$ blanket. After 2 days, a further 20 ml of toluene were added, and after a further 2 days, a further 0.20 g of diethylene glycol 9,9-bis(2-ethylhexyl)fluorene-2,7-bisboronate were added. After a further 6 hours, 0.5 ml of 4-bromofluorobenzene was added, and the mixture was refluxed for a further 3 hours.

Work-up was carried out as described under Example P1, giving 3.85 g (9.9 mmol, 33%) of polymer C1 a pale beige solid.

$^1$H-NMR ($CDCl_3$): [ppm] δ=7.9–7.3 (m, 6H, H-aromatic); 2.15 (br. s, 4H, C(9)—$CH_2$); 1.1–0.4 (m, 30H, H-alkyl). GPC: THF+0.25% oxalic acid; column set SDV500, SDV 1000, SDV10000 (PPS), 35° C., UV detection 254 nm: $M_w$=70000 g/mol, $M_n$=34000 g/mol. UV-VIS (film): $\lambda_{max}$=376 nm; PL (film): $\lambda_{max}$=420 nm, 444 nm.

C) Measurements

Whereas polymer C1 gave green-yellow emission (maximum at about 540 nm) in a typical EL device, polymer P1 according to the invention exhibited strong blue luminescence (wavelength at about 460 nm). This color remained constant even during an extended observation time.

What is claimed is:

1. A conjugated polymer which contains structural units of the formula

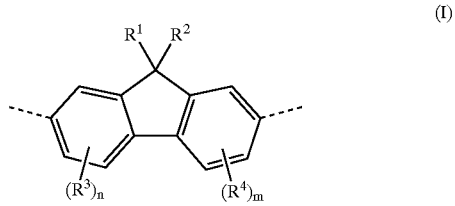

(I)

in which $R^1$ and $R^2$ are two different substituents selected from the group consisting of $C_2$–$C_{40}$-heteroaryl and $C_5$–$C_{40}$-aryl, wherein said aryl and said heteroaryl independently of one another are optionally substituted by one or more substituents $R^3$, $R^3$ and $R^4$ are identical or different and are $C_1$–$C_{22}$-alkyl, $C_2$–$C_{20}$-heteroaryl, $C_5$–$C_{20}$-aryl, F, Cl, CN, $SO_3R^5$ or $NR^5R^6$, wherein said alkyl is branched, unbranched or alternatively is cycloalkyl radical, and individual, non-adjacent $CH_2$ group(s) of the alkyl radical are optionally replaced by O, S, C=O, COO, N—$R^5$ or a simple aryl, wherein the above mentioned said aryls are optionally substituted by one or more non-aromatic substituents $R^3$, $R^5$ and $R^6$ are identical or different and are H, $C_1$–$C_{22}$-alkyl, $C_2$–$C_{20}$-heteroaryl or $C_5$–$C_{20}$-aryl, wherein said alkyl is branched or unbranched or alternatively is a cycloalkyl radical, and individual, non-adjacent $CH_2$ group(s) of the alkyl radical is optionally replaced by O, S, C=O, COO, N—$R^5$ or a simple aryl radical, wherein the above mentioned said aryls are optionally substituted by one or more non-aromatic substituents $R^3$ and m and n are each identical or different and are an integer 0, 1, 2 or 3.

2. The polymer as claimed in claim 1, wherein the polymer contains at least 10 mol % of structural units of the formula (I) incorporated randomly, alternately, periodically or in blocks.

3. The polymer as claimed in claim 1, which comprises from 10 to 10,000 recurring structural units of the formula (I).

4. The polymer as claimed in claim 1, wherein m and n are zero.

5. An organic semiconductor which comprises the polymer as claimed in claim 1.

6. An electroluminescent device containing the polymer as claimed in claim 1.

7. A compound of the formula (A)

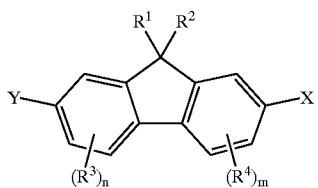

in which
R$^1$ and R$^2$ are two different substituents selected from the group consisting of C$_2$–C$_{40}$-heteroaryl and C$_5$–C$_{40}$-aryl, wherein said aryl and said heteroaryl independently of one another are optionally substituted by one or more substituents R$^3$, R$^3$ and R$^4$ are identical or different and are C$_1$–C$_{22}$-alkyl, C$_2$–C$_{20}$-heteroaryl, C$_5$–C$_{20}$-aryl, F, Cl, CN, SO$_3$R$^5$ or NR$^5$R$^6$, wherein said alkyl is branched, unbranched or alternatively is a cycloalkyl, and individual, non-adjacent CH$_2$ group(s) of the alkyl radical is optionally replaced by O, S, C=O, COO, N—R$^5$ or a simple aryl radical, wherein said above mentioned aryls are optionally substituted by one or more non-aromatic substituents R$^3$, R$^5$ and R$^6$ are identical or different and are H, C$_1$–C$_{22}$-alkyl, C$_2$–C$_{20}$-heteroaryl or C$_5$–C$_{20}$-aryl, wherein said alkyl is branched or unbranched or alternatively is a cycloalkyl, and individual, non-adjacent CH$_2$ group(s) of the alkyl radical is optionally replaced by O, S, C=O, COO, N—R$^5$ or a simple aryl radical, wherein said above mentioned aryls are optionally substituted by one or more non-aromatic substituents R$^3$, m and n are identical or different and are each an integer 0, 1, 2 or 3 X and Y are identical or different and are halogen, B(OR$^7$)$_2$ or SnR$^7$R$^8$R$^9$, and R$^7$, R$^8$ and R$^9$ are identical or different and are H or C$_1$–C$_6$-alkyl, wherein two radicals optionally form a common ring and these radicals are optionally branched or unbranched.

8. The polymer as claimed in claim 1 wherein R$^1$ and R$^2$ are two different substituents wherein each is a C$_6$-aryl substituted by one or more substituents R$^3$ wherein R$^3$ is alkyl and said individual nonadjacent CH$_2$ group(s) of the alkyl radical are optionally replaced by O.

9. The compound as claimed in claim 7 wherein R$^1$ and R$^2$ are two different substituents wherein each is a C$_6$-aryl substituted by one or more substituents R$^3$ wherein R$^3$ is alkyl and said individual nonadjacent CH$_2$ group(s) of the alkyl radical are optionally replaced by O.

10. The compound as claimed in claim 7 wherein m and n are 0.

* * * * *

UNITED STATES PATENT AND TRADEMARK OFFICE
CERTIFICATE OF CORRECTION

PATENT NO.     : 6,653,438 B1                                          Page 1 of 1
DATED          : November 25, 2003
INVENTOR(S)    : Hubert Spreitzer et al.

It is certified that error appears in the above-identified patent and that said Letters Patent is hereby corrected as shown below:

<u>Title page,</u>
Item [75], "Heinrich Becker Zum" should read -- Heinrich Becker --.

Signed and Sealed this

Second Day of March, 2004

JON W. DUDAS
*Acting Director of the United States Patent and Trademark Office*